United States Patent [19]

Deutsch et al.

[11] 4,361,537
[45] * Nov. 30, 1982

[54] TEST DEVICE AND METHOD FOR ITS USE

[75] Inventors: Marshall E. Deutsch, Sudbury; Louis W. Mead, Lexington, both of Mass.

[73] Assignee: Thyroid Diagnostics, Inc., Bedford, Mass.

[*] Notice: The portion of the term of this patent subsequent to Nov. 25, 1997, has been disclaimed.

[21] Appl. No.: 177,281

[22] Filed: Aug. 11, 1980

Related U.S. Application Data

[60] Continuation of Ser. No. 3,076, Jan. 12, 1979, Pat. No. 4,235,601, which is a continuation of Ser. No. 887,886, Mar. 20, 1978, abandoned, which is a division of Ser. No. 701,762, Jul. 2, 1976, Pat. No. 4,094,647.

[51] Int. Cl.³ ............................................. G01N 33/52
[52] U.S. Cl. ........................................ 422/56; 422/71
[58] Field of Search ............... 23/230 R, 230 B, 230.3, 23/230.6; 422/55, 56, 71; 435/28

[56] References Cited

U.S. PATENT DOCUMENTS

| | | | |
|---|---|---|---|
| 3,011,874 | 12/1961 | Deutsch et al. | 422/57 |
| 3,376,114 | 4/1968 | Eberle | 23/230.6 |
| 3,420,205 | 1/1969 | Morison | 422/56 X |
| 3,776,698 | 12/1973 | Eisentraut | 23/230 B |
| 3,888,808 | 6/1975 | Bagshawe | 23/230 B |
| 3,893,808 | 7/1975 | Campbell | 422/56 X |
| 3,895,914 | 7/1975 | Alberty et al. | 23/253 TP |
| 3,902,847 | 9/1975 | Busch et al. | 422/56 X |
| 3,915,647 | 10/1975 | Wright | 422/56 |
| 3,932,133 | 1/1976 | Ishikawa | 422/55 |
| 3,966,897 | 6/1976 | Renn et al. | 424/1.5 |
| 3,980,437 | 9/1976 | Koshimoto et al. | 422/55 |
| 4,094,647 | 6/1978 | Deutsch et al. | 422/56 |
| 4,235,601 | 11/1980 | Deutsch et al. | 23/230 R |

FOREIGN PATENT DOCUMENTS 837896  5/1976  Belgium .

*Primary Examiner*—Arnold Turk

[57] ABSTRACT

A test device for determining a characteristic of a sample, particularly for determining substances in fluid samples. The device comprises a strip element which is composed of a material capable of transporting a developing fluid therealong by capillarity and which has a portion at a predetermined location on the strip element for receiving the test sample and portions at predetermined locations on the strip element incorporated with reagent means for providing a detectable response sensitive to the characteristic under determination. The beginning end portion of the strip element is immersed in the developing fluid which, as a result, traverses the length on the strip element, thereby promoting appropriate contact between the test sample and the reagent means resulting in the disposition of a detectable response at a predetermined location on the strip element, which response is a function of the characteristic under determination. The test device is particularly suited for performing binding assays, in particular those wherein a radioisotope is used as a label, such as radioimmunoassays.

21 Claims, 9 Drawing Figures

TEST DEVICE AND METHOD FOR ITS USE

This is a continuation of application Ser. No. 3,076, filed Jan. 12, 1979, and which issued Nov. 25, 1980, as U.S. Pat. No. 4,235,601, which is a continuation of application Ser. No. 887,886 filed Mar. 20, 1978, and now abandoned, which is a division of application Ser. No. 701,762, which was filed July 2, 1976, and which issued June 13, 1978, as U.S. Pat. No. 4,094,647.

BACKGROUND OF THE INVENTION

1. Field of the Invention

This invention relates to test devices and methods for their use in detecting a characteristic of a sample. In particular, the present invention relates to test devices and methods for their use in performing binding assays such as for determining a ligand in or the liquid binding capacity of a fluid sample, such as a sample of a biological liquid. In preferred embodiment, the present invention relates to test devices for performing binding assays in which a radioisotope is used as a label.

2. Brief Description of the Prior Art

Test devices in the form of test strips have become commonplace in the analysis of various types of samples, such as liquid samples in the nature of industrial fluids, biological fluids, and so forth, because of the convenience and speed of their use. Test strips designed for detecting various clinically significant substances in biological fluids, such as urine and serum, in particular have been found to be very advantageous in assisting the diagnosis and treatment of diseased states in man and other animals.

Conventional test strips generally comprise an absorbent or porous matrix incorporated with indicator reagents, usually of a colorimetric type. The sample to be tested is contacted with the reagent matrix, such as by momentary immersion where the sample is liquid, and the indicator response is observed after a set period of time. Such test strips have the limitation that where more than one chemical reaction is involved, all of the test reactions must be mutually compatible since they all occur in the presence of each other in the reagent matrix.

Recently, certain test strips have been developed which allow several test reactions to take place in a predetermined sequence. U.S. Pat. No. 3,011,874 discloses a test strip representative of this type. The disclosed strip comprises a paper strip partitioned widthwise into various bands, first a blank band for immersion in a liquid test sample, followed successively by a reaction band, a gas liberation band, a barrier band, and an indicator band. However, there still exists a long-felt and recognized need for further improvement.

First of all, the conventional test strips have limited sensitivity. Because the detectable response produced by the conventional strips is almost always a color change, limited color resolution of the eye, and spectrometers as well, does not allow conventional test strips to detect substances, such as hormones, vitamins, and the like, which appear in body fluids at concentrations below 0.1 mg/ml. Secondly, a relatively large sample volume must be provided in order to wet the entire reagent matrix of the conventional test strips. The use of the test strip described in the aforementioned U.S. Pat. No. 3,011,874 requires a sample volume sufficient to wet by capillary absorption all of the strip up to the barrier band.

The known analytical methods for detecting substances which occur in samples in small amounts are based on the binding affinity of such substances for certain synthetic or naturally produced binding agents. The most commonly used binding assay at the present time is probably the radioimmunoassay in which the substance to be determined competes under controlled conditions with a radiolabeled form of itself for binding to a limited quantity of specific antibody. The proportion of the radiolabeled form that successfully binds to antibody to that which remains in a free state is a function of the amount of the substance under determination in the test sample. Because binding assay methods require accurate and timed addition of minute quantities of reagents, the state of the art is that of time consuming and burdensome wet chemistry. The association of binding assay techniques with test devices which attempt to simplify and reduce the cost of such assays has been extremely limited despite the fact that many hundreds of technical papers have appeared in the literature over the past two decades relating to radioimmunoassay approaches alone.

U.S. Pat. No. 3,888,629 describes a device wherein the binding reaction takes place in a disc-shaped matrix pad held in a section of a column. Free and bound label are separated by fitting a wash reservoir column section above the pad containing section and a column section containing an absorbent material below the pad containing section. As the wash solution is drawn through the reaction pad, free label is carried along by the wash leaving the bound label behind because of the filtration properties of the reaction pad. This device would be cumbersome and awkward to use and requires several time consuming manipulative steps.

German Offenlegungsschrift No. 2,241,646 discloses a complex automated instrument for performing radio-immunoassays wherein the binding reagents, i.e. the label and specific antibody, and an aliquot of the liquid to be tested are dispensed onto a cellulose strip at discrete locations. After an incubation period, the test areas on the strip are washed by drawing a liquid therethrough by suction, thereby removing free label. The level of radioactivity remaining at each test area is then measured and related to the amount of unknown in the sample. In addition to requiring the use of an expensive and complex instrument, this method requires controlled dispensing of reagents and timing of incubations, the same as the conventional wet chemistry methods.

It is therefore an object of the present invention to provide a novel test device capable of application to analytical methods wherein a set of sequential test reactions is involved and wherein a minute sample size may be used.

It is a further object of the present invention to provide a test device capable of application to analytical methods having sensitivities below 0.1 mg/ml.

It is a particular object of the present invention to provide a test device useful in performing binding assays to detect characteristics of fluid samples wherein the user is not required to dispense any of the binding reagents or to carefully time incubation periods and particularly wherein radioactive labels are employed, such as in radioimmunoassays.

SUMMARY OF THE INVENTION

The present invention provides a test device which satisfies the aforesaid objectives, such device comprising an elongated strip element composed of a material capable of transporting a developing fluid longitudinally therealong by capillarity. One of the end portions of the strip element is designated the beginning end portion, and the other, the terminal end portion, to reflect the fact that the travel of the developing fluid along the strip element begins by immersion or other contact of the developing fluid with the beginning end portion and such travel terminates when the leading front of the developing fluid reaches the terminal end portion. The strip element has a portion designated or marked for receiving the sample to be tested and is incorporated at one or more portions with reagent means comprising one or more reagent constituents. All of the constituents of the reagent means may be incorporated with a single discrete portion of the strip element, some of the reagent constituents may be incorporated in combination with a single discrete portion of the strip element with the remaining reagent constituents being incorported, singularly or in any appropriate combination, with one or more discrete portions of the strip element, or each of the reagent constituents may be incorporated with separate portions of the strip element. The sequence of the various reagent constituent incorporated portions of the strip element and the sample receiving portion thereof, as well as the spacing therebetween, is established such that upon complete traversal of the strip element by the developing fluid, a detectable response which is a function of the characteristic under determination is disposed at a predetermined measuring location on the strip element.

DESCRIPTION OF THE PREFERRED EMBODIMENTS

Figure 1:
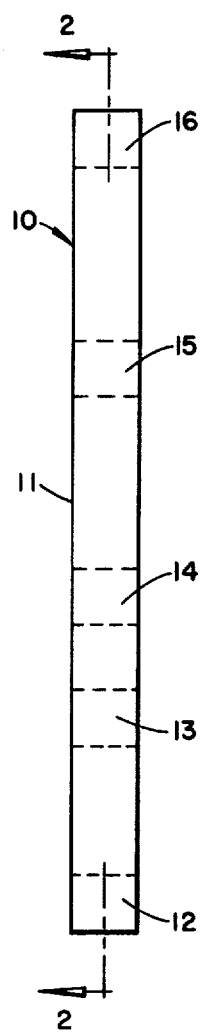
FIGS. 1, 3, and 5, respectively, are front plan views of three different forms of the test device of the present invention.
Figure 2:
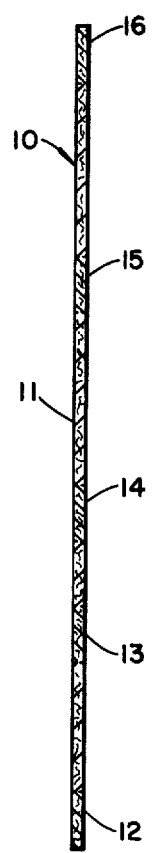
FIG. 2 is a cross-sectional view of the test device shown in FIG. 1 taken along line 2—2.

Referring to the drawing, FIGS. 1 and 2 depict a test device 10 comprising a strip element 11 composed of a material, usually bibulous paper, which is absorbent relative to a selected developing fluid, usually an aqueous solution. Strip element 11 has a beginning end portion 12 and a terminal end portion 16. A sample receiving portion 13 is designated on strip element 11 by appropriate marking means such as a dried spot of a dye solution. Portions 14 and 15 of strip element 11 are incorporated with appropriate constituents of a reagent means selected for detecting a particular characteristic of a test sample. In use, the sample to be tested is dispensed on sample receiving portion 13 of strip element 11 and beginning end portion 12 is immersed in the developing fluid which then begins to advance along strip element 11 by capillarity towards terminal end portion 16. The developing fluid is selected so that the dispensed sample and the constituents of the reagent means are appropriately combined as the developing fluid traverses strip element 11. When the leading front of the developing fluid reaches terminal end portion 16, a detectable response of the reagent means which is related to the characteristic to be determined is disposed at a predetermined measuring location on strip element 11, such as at portion 15. Such response is then measured by appropriate means, for example, by measuring a chemical or physical property of such portion. For instance, if the detectable response of the reagent means is a physical property such as fluorescence, light absorbance, or radioactivity, that property can be measured on the intact strip element. Also, if the detectable response is a chemical property, such as the appearance of a chemical product or the disappearance of a chemical reactant, such property can be measured by adding an indicator to the measuring location on the strip element or by first separating the measuring location from the remainder of the strip element and making appropriate measurements and/or reagent additions. Where the response is measured on the intact strip element, for example at portion 15, it is useful to appropriately mask all of the remaining surface of the strip element to assure that the measured response is only that associated with the measuring location, i.e. portion 15. As masking agent may be used, a shroud which is opaque to the physical property being measured and which has an opening for registry with portion 15. Preferably an indicator means responsive to contact with the developing fluid is incorporated with terminal end portion 16 to signal completion of the test. It is also preferred that the volume of developing fluid into which beginning end portion 12 is immersed be equal to the precise volume of developing fluid that is taken up by strip element 11 upon arrival of the leading edge of the developing fluid at terminal end portion 16, thereby resulting in the automatic termination of the transport of the developing fluid at the proper time.

In one embodiment of the test device of the present invention for determining a ligand in a fluid sample, the reagent means comprises appropriate binding reagents including a specific binding partner, such as an antibody or other binding protein, for the ligand and a label comprising a labeled form of the ligand or of a binding analog thereof. Predetermined quantities of the label and the specific binding partner, the latter in an immobilized form, are incorporated with portions 14 and 15 respectively. In use, as the developing fluid advances along strip element 11, the sample and the label are mixed and transported into contact with the immobilized binding partner whereupon the label and any ligand in the sample compete for binding to the binding partners. The fraction of the label which successfully becomes bound to the binding partners thereby becomes immobilized at portion 15. As the developing fluid advances to terminal end portion 16, the unbound, or free, fraction of the label is transported a distance away from portion 15. The amount of label immobilized at portion 15 is then measured appropriately and is related to the amount of ligand in the test sample. It is particularly useful to use as the label a radioactive form of the ligand or of a binding analog thereof. If the radioactive label is an iodine isotope, an additional advantage of the test device results in that contamination in the form of radioactive free iodide does not interfere with measurements at portion 15 since such is transported a distance away from portion 15 by the advance of the developing fluid.

Figure 3:
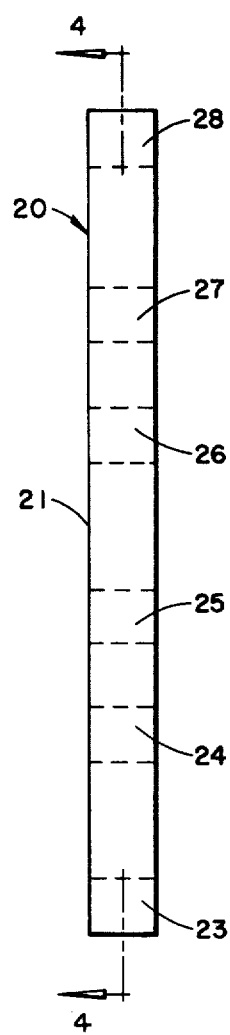
Figure 4:
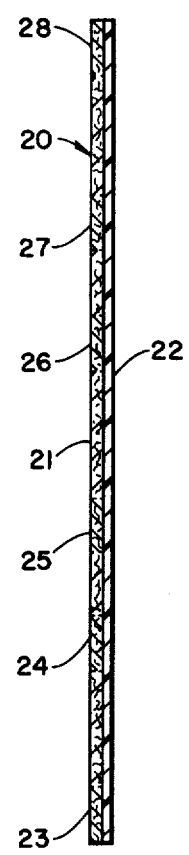
FIG. 4 is a cross-sectional view of the test device shown in FIG. 3 taken along line 4—4.

A variation of the test device described in the next preceeding paragraph is illustrated in FIGS. 3 and 4 of the drawing. Test device 20 comprises a strip element 21 affixed to an inert support strip 22, usually made of a semi-rigid plastic, and having a beginning end portion 23, a terminal end portion 28, and a sample receiving portion 25, which in this embodiment is situated between reagent means incorporated portions 24 and 26. Portion 24 of the strip element is incorporated with the label and portion 26 is incorporated with the specific binding partner, which in this embodiment is not immobilized relative to the developing fluid but rather is transportable thereby. In use, the sample and label are mixed by the advancing developing fluid and competitive binding for the binding partner occurs at portion 26. As the developing fluid advances farther, the resulting label-binding partner complexes are transported along strip element 21 along with the sample and free label, however, such complexes advance at a slower rate than that at which free label is carried. When the leading front of the developing fluid reaches terminal end portion 28, the label-binding partner complexes are disposed at portion 27 while free label has been carried farther towards terminal end portion 28. Measurement can then be made at portion 27 of strip element 21. Alternatively, portion 27 can be incorporated with an immobilized agent for the label-binding partner complexes, such as a second antibody or a protein precipitating agent, in order to assure localization of such complexes at portion 27.

A preferred form of the test device of the present invention is illustrated in FIGS. 5-9 of the drawing. Test device 30 comprises a strip element 51 folded widthwise over one end of an inert support strip 32 in such a manner that the transverse edge of beginning end portion 33 of strip element 31 is about even with the other edge of support 32 and the transverse edge of terminal end portion 37 of strip element 31 is spaced a distance short of the same edge of support 32. Sample receiving portion 34 and reagent means incorporated portions 35 and 36 correspond to portions 13, 14, and 15, respectively, of test device 10 depicted in FIGS. 1 and 2. For example, for using test device 30 to detect a ligand in a liquid sample, portion 35 may be incorporated with a label and portion 36 with an immobilized binding partner. In this embodiment, test device 30 functions in a similar manner to test device 10 with the predetermined measuring location being disposed at portion 36.

Figure 8:
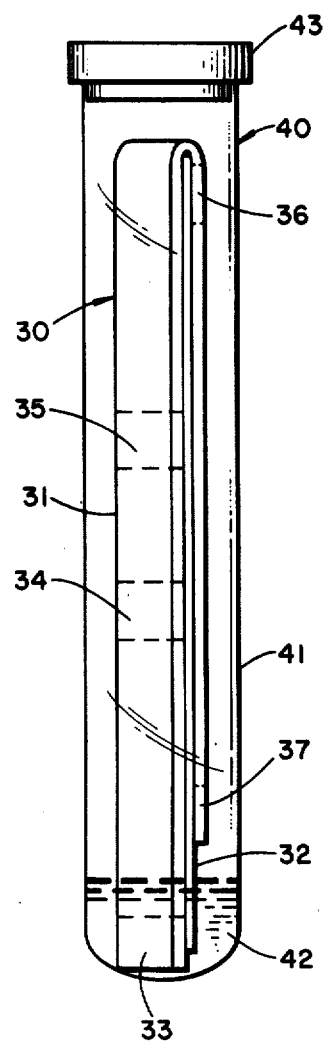
FIG. 8 is a perspective view of an assembly comprising the test device depicted in FIGS. 5-7 enclosed in a sealed chamber with the device in contact with a volume of developing fluid.

FIG. 8 illustrates an operative mode of a preferred test means 40 of the present invention. After the test sample has been dispensed onto sample receiving portion 34 of the strip element 31, test device 30 is inserted, with beginning end portion 33 down, into test tube 41 which contains a volume of a developing fluid 42. The size of test tube 41 and the dimensions of strip element 31 are selected preferably so that the volume of developing fluid 42 is precisely the amount that is taken up by strip element 31 upon arrival of the leading edge of developing fluid 42 at terminal end portion 37 and so that terminal end portion 37 remains out of contact with developing fluid 42 when test device 30 is initially inserted into tube 41. After sample inoculated test device 30 is inserted into tube 41, friction cap 43 is fitted onto tube 41 to form a sealed chamber to prevent evaporation of developing fluid 42 during the traversal thereof along strip element 31.

Figure 9:
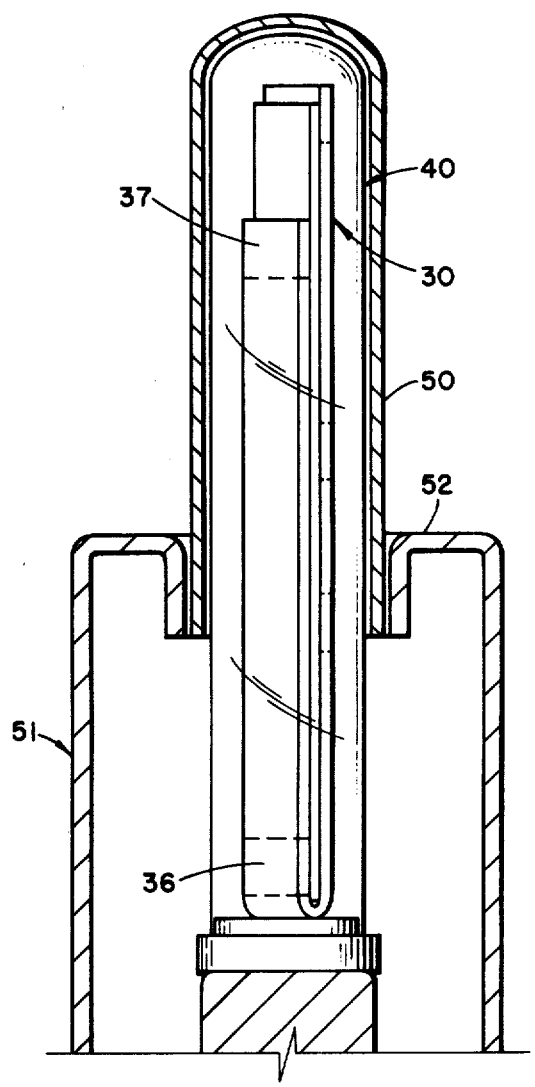
FIG. 9 is a perspective view in partial cross-section of the assembly depicted in FIG. 8 inverted and positioned in a well of an instrument for measuring the response of the reagent means.

FIG. 9 depicts a preferred manner of measuring the reagent means response at portion 36 of strip element 31. It can be seen that by positioning sample receiving portion 34 and reagent means incorporated portions 35 and 36 appropriately on strip element 31 so that the measuring location is at or proximate to the fold in strip element 31, measurement of the reagent means response can be conveniently accomplished by masking all of strip element 31 other than the portion proximate to the fold of strip element 31. Test means 40 is inserted into shroud 50 which is opaque to the physical property characterizing the response of the reagent means. The resulting assembly is inverted and placed into well 52 of instrument means 51 for measuring the reagent means response.

While the test device of the present invention is particularly suited for use in performing binding assays as discussed previously, various other types of assay methods can be carried out using the test device. Conventional colorimetric assays may be carried out by selecting appropriate reagent means and appropriately orienting the reagent constituents thereof and a sample receiving portion along the strip element such that the desired color response is disposed at a predetermined measuring location upon completion of the test. In such an assay, the test device offers the advantage of accommodating sequential test reactions and has a high degree of accuracy because of the use of a precisely dispensed aliquot of the test sample.

As a further example of the diverse types of assays that can be performed using the test device of the present invention, there will now be described a test device for quantitatively determining proteins in a fluid sample. Referring to FIGS. 3 and 4 of the drawing, strip element 21 is provided with sample receiving portion 24 with portions 25 and 26 being incorporated, respectively, with a label and with an agent for coupling the label to proteins. As example of a label/coupling agent combination is radioactive iodide and 1,3,4,6-tetrachloro-3α,6α-diphenyl glycoluril (sold as IODO-GEN by Pierce Chemical Co., Rockford, Ill.). The capillary advance of the developing fluid mixes the test sample and the label, and when the resulting mixture enters portion 26, the label is chemically coupled to proteins in the sample forming labeled derivatives. As the developing fluid advances farther, the labeled derivatives and free label are separated by their differing rates of transport along strip element 21 by the developing fluid. Upon complete traversal of strip element 21 by the developing fluid, the label response in the area of strip element 21 at which are disposed the labeled derivatives provides a measure of the protein content of the sample. This type of test device can also be used to quantitatively determine a particular protein by positioning the coupling agent incorporated portion of the strip element a predetermined distance from the measuring location, i.e. positioning portion 26 a predetermined distance from portion 27, where such predetermined distance corresponds to the distance that the labeled derivative of the protein of interest is transported during the time that the developing fluid travels from the coupling agent incorporated portion to the terminal end portion of the strip element, i.e. portion 28. The measuring point, i.e. portion 27, will then contain the labeled derivative of the protein of interest only.

Figure 5:
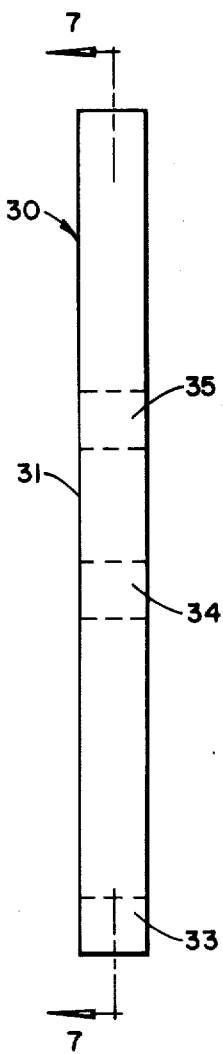
Figure 6:
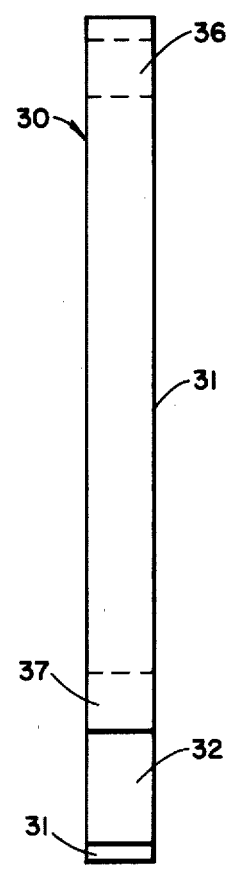
FIG. 6 is a rear plan view of the test device depicted in FIG. 5.
Figure 7:
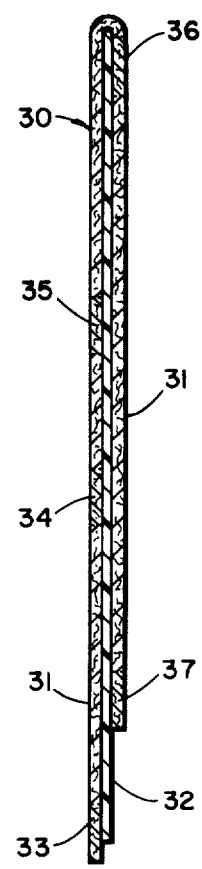
FIG. 7 is a cross-sectional view of the test device shown in FIG. 5 taken along line 7—7.

The test device of the present invention can also be designed to quantitatively determine substances which react with a reagent system to produce hydrogen peroxide. Referring to FIGS. 5-7 of the drawing, strip element 31 is provided with sample receiving portion 34 and portions 35 and 36 are incorporated, respectively, with radioactive iodide and with the aforementioned reagent system. A preferred reagent system includes an oxidase enzyme specific for the substance to be determined. For example, to detect glucose or cholesterol, the reagent system would comprise glucose oxidase or cholesterol oxidase, respectively. In use, the developing fluid mixes the sample and radioactive iodide. When the mixture contacts the reagent system, hydrogen peroxide is produced in proportion to the amount of the substance to be determined present in the sample with an attendant proportional conversion of radioactive iodide to radioactive iodine, the latter being strongly adsorbed by strip element 31. As the developing fluid advances, the remaining radioactive iodide is separated from the adsorbed radioactive iodine. The final location of either radioactive species upon completion of the test can be the measuring location.

With reference to the particular embodiments of the test device of the present invention described hereinabove and in the Examples to follow, the present test device is applicable to the determination of a characteristic of a sample and comprises (a) a strip element, usually elongated, having a beginning end portion and a terminal end portion and having a portion for receiving said sample positioned at a predetermined location thereon, said strip element being composed of a material capable of transporting a developing fluid, usually longitudinally, therealong by capillarity, and (b) reagent means incorporated with said strip element at at least one predetermined location thereon for providing a detectable response, as a function of the characteristic under determination, at a predetermined measuring location on said strip element upon traversal thereof by said developing fluid from said beginning end portion to said terminal end portion. The choice of the material composing the strip element, the composition of the developing fluid, the dimensions of the strip element, and the orientation of the sample receiving portion of the strip element and the portion or portions incorporated with the reagent means will, of course, depend upon the characteristic to be determined and the selected reagent means.

The strip element may be made of any material which is insoluble in the developing fluid and which is capable of transporting the developing fluid by capillarity. The strip element typically is relatively flexible while having a satisfactory wet strength to stand up under use. Of course, it should be made of a material which will not deleteriously affect the interactions between the developing fluid, the test sample, and the reagent means. A particularly useful material for the strip element is bibulous paper, such as filter paper, since the developing fluid is usually aqueous in nature, however, other materials may also be used, including various felts, cloths, gels, membranes, and films made of natural or synthetic substances including polymers. While the length and width of the strip element may vary widely, the thickness of the strip element is usually between about 0.008 inch (0.2 mm) and 0.04 inch (4.0 mm).

The strip element is preferably affixed to an inert support for mechanical strength. Usually, the strip element and inert support are joined in laminate fashion with both being of approximately equal width. The thickness of the inert support may vary depending on the rigidity of the material of which it is made. Exemplary materials are the various vinyl plastics as well as polyester, polycarbonate, methyl methacrylate polymer, polystyrene, polyethylene, polypropylene, and waxed cardboard. The length of the inert support will vary depending upon the desired configuration of the test device. The inert support may be approximately the same length as the strip element (as shown in FIGS. 3 and 4 of the drawing) or, as is particularly preferred, may have a length greater than 0.5 times but less than 1.0 times the length of the strip element in order that the transverse edge of the beginning end portion of the strip element may be even with or slightly extended over one end of the support and the strip element folded widthwise over the other end of the support with the transverse edge of the terminal end portion of the strip element being a spaced distance from the first mentioned end of the support (as shown in FIGS. 5-7 of the drawing). The latter mentioned preferred configuration is most advantageous when the orientation of the sample receiving portion and the reagent means incorporated portion or portions are established such that the predetermined measuring location is at or proximate to the fold in the strip element. This allows convenient measurement of the reagent means response at the measuring location by masking all but a minor portion of the strip element proximate to the fold.

The terminal end portion of the strip element is preferably incorporated with indicator means responsive to the developing fluid to serve as a signal that the traversal of the strip element by the developing fluid is complete. For example, the indicator means may comprise a colorimetric reagent composition sensitive to a solvent or solute of the developing fluid. Where the developing fluid is aqueous, the indicator means may contain a water sensitive reagent such as cobalt chloride and, in such case, the indicator means may also serve as a stability indicator. Also, the indicator means may comprise all of the components of a colorimetic reaction activated by the developing fluid. For example, where the developing fluid is aqueous, the indicator means may include an acidic or basic material and a pH indicator.

The developing liquid must be capable of traversing the strip element by capillarity and have solvent properties appropriate for the desired combination of the test sample and reagent means during such traversal. Usually, the developing solution is a solvent for appropriate substances in the test sample, such as a substance to be detected and contains various ancillary agents such as stabilizing agents, preservatives, and inhibitory agents against interfering reactions.

Where a constituent of the reagent means is required to be incorporated with a portion of the strip element in an immobilized state, such may be accomplished in any conventional manner. For example, the constituent may be immobilized by physical adsorption or chemical coupling to the strip element. An alternative method is to render the constituent insoluble and immovable by the developing fluid such as by associating it by physical or chemical means with a large insoluble particle. For example, where a binding assay test device is involved and one of the reagent constituents is a protein, such as an antibody, such can be immobilized effectively by absorption to plastic beads.

In the case of a test device comprising reagent means that includes a label, such as where a binding assay is to be performed, such label may be any chemical substance or moiety having a detectable characteristic which is unique compared to the other materials involved in carrying out the test. For instance, such label may have fluorescent or distinguishable light absorption properties or reactivity. Particularly preferred are substances which are radioactive because of the high degree of sensitivity at which such can be detected. Radioactive labels, particularly radioactive iodine such as $^{125}$I and $^{131}$I, are particularly useful in carrying out binding assays using the test device of the present invention. While radioactive labels incorporated with a ligand or a binding analog thereof elicit a measurable characteristic which is the same no matter whether such ligand or analog is bound to a binding partner or not, it is contemplated that labels may be used which as incorporated with the ligand or analog yield characteristics which are measurably different when the ligand or analog is in its bound state than when it is in its free state.

As applied to binding assays, the present test device can be designed to detect any ligand for which there is a specific binding partner. The ligand usually is a peptide, protein, carbohydrate, glycoprotein, steroid, or other organic or inorganic molecule or ion for which a specific binding partner exists in biological systems or can be synthesized. The ligand, in functional terms, is usually selected from the group consisting of antigens and antibodies thereto; haptens and antibodies thereto; and hormones, vitamins, metabolites and pharmacological agents, and their receptors and binding substances. Specific examples of ligands which may be detected using the present invention are hormones such as insulin, chorionic gonadotropin, thyroxine, triiodothyronine, estriol, testosterone, androsterone, equilenin, estrone, progesterone, pregnenolone, cortisol, 17-hydroxydeoxy-corticosterone, and aldosterone, pharmacological agents and their metabolites such as dilantin, digoxin, morphine, digitoxin, barbiturates, catecholamines, glutethimide, cocaine, diphenylhydantoin, meprobamate, benzdiazocycloheptanes, and phenothiazines; antigens and haptens such as ferritin, bradykinin, prostoglandins, hemoglobin, enzymes, myoglogin, and tumor specific antigens, vitamins such as biotin, the B vitamin group, vitamin A, the D vitamins, vitamins E and K, folic acid, and ascorbic acid; binding proteins such as antibodies, thyroxine binding globulin, avidin, intrinsic factor, and transcobalamin; and other substances including antibodies, pesticides, fungicides, nematocides, living or non-living cells derived from bacteria, protozoa, fungi, viruses, and high order animals, and minerals such as calcium, ferrous and ferric ions, and oxalate, phosphate, and chloride ions.

In addition to the detection of particular substances of groups of substances in a test sample, other characteristics may be determined using the present device. For example, ligand binding capacities may be determined where a ligand exists in the sample in a free form and a bound form. The ligand binding capacity of the sample is the amount or percent of exogenous free form ligand that is converted into the bound form when added to the sample (such as triiodothyronine binding capacity as involved in Example 2 hereof).

In most instances, the test reactions can be carried out successfully at room temperature but, in general, the temperature at which the test is performed may range from about 3° C. to about 45° C. with the reaction rate being generally directly related to the temperature.

The test sample may be a solid material but usually is a naturally occurring or artificially formed liquid suspected of containing or known to contain the substance or characteristic to be determined. The present test device is particularly suited to assay biological fluids, or dilutions or other treatments thereof, such as serum, plasma, urine, and amniotic, cerebral, and spinal fluids. Solid matter, such as tissue or cells, or gases may be tested also by reducing them to a liquid form such as by dissolution of the solid or gas in a liquid or by liquid extraction of a solid.

The present invention will now be illustrated, but is not intended to be limited, by the following Examples.

EXAMPLE 1

Test for Thyroxine in Serum

A. Preparation of Test Devices

A sheet of filter paper (Whatman #17 from W. & R. Balston Ltd. Maidstone, Kent, England) was cut into strips measuring 188 mm in length and 6 mm in width. Each paper strip was folded widthwise over one end of a plastic strip 0.015 inch (0.38 mm) thick, 4 inches (102 mm) long, and ¼ inch (6.3 mm) wide, in such a fashion that one end of the paper strip (designated the beginning end) was about even with one end of the plastic strip, leaving the other end of the paper strip (designated the terminal end) about ¾ inch (19 mm) short of the same end of the plastic strip on the reverse side thereof. The folded paper strip was affixed to the plastic strip by means of the double-faced adhesive tape.

The following liquid mixtures were prepared:

Mixture A—A mixture of:
(1) 0.2 ml goat antiserum raised against a conjugate of thyroxine and human serum albumin (the antiserum was raised in a manner similar to that described in J. Clin. Endo. 33: 509-16(1971) );
(2) 0.4 ml of an aqueous suspension of polystyrene beads containing 10% solids consisting of beads with an average diameter of 0.11μ (micron) (supplied by Sigma Chemical Co., St. Louis, MO);
(3) 2.4 ml of a 100 ml aqueous solution containing 694 mg potassium dihydrogen phosphate, 509 mg disodium phosphate heptahydrate, 200 mg thimerosal (obtained from K&K Labs, Plainview, NY) and 0.5 mg crystal violet;
(4) 0.2 ml of 5% aqueous sodium lauryl sulfate;
(5) 20 μl (microliters) of an aqueous solution containing 50 mg gentamicin manufactured by Schering Corp., Bloomfield, NJ per ml; and
(6) a trace (about 1 μl) of silicone antifoam (AF 60 emulsion grade manufactured by General Electric and obtained from Harwick Standard Chemical Co., Boston, MA).

Mixture B—A mixture of:
(1) 20 microcuries $^{125}$I-labeled thyroxine (obtained from Cambridge Radiopharmaceuticals Corp., Billerica, MA) in 0.2 ml of 50% propylene glycol (specific activity of about 600 microcuries per mg);
(2) 3 ml of a 100 ml aqueous solution containing 5.32 g sodium barbital, 1.44 ml 2 N hydrochloric acid, 400 mg thimerosal, 10 mg disodium ethylenediamine tetraacetate, and 0.5 mg crystal violet;
(3) 8 μl of an aqueous solution containing 50 mg gentamicin per ml; and (4) 8 μl of an aqueous solution containing 250 mg human serum albumin per ml.

Mixture C—An aqueous solution containing 400 mg/100 ml thimerosal and 10 mg/100 ml of red dye Ponceau S.

Mixture D—An aqueous solution containing 0.05 M hydrochloric acid and 50 mg/100 ml bromocresol purple.

The above liquid mixtures were then applied dropwise to the paper strips as follows:

| Mixture | Volume (μl) | Point of application measured from beginning end of strip (mm) |
|---|---|---|
| A | 20 | 108 |
| B | 20 | 80 |
| C | 10 | 60 |
| D | 10 | 185 |

The strips were allowed to dry at room temperature.

A developing fluid was prepared to consist of 100 ml of an aqueous solution containing 5.32 g sodium barbital, 1.44 ml 2 N hydrochloric acid, 400 mg thimerosal, and 10 mg disodium ethylenediamine tetraacetate.

Referring to FIGS. 5–7 of the drawing, the resulting test devices 30 each included (a) sample receiving portion 34 (point of application of Mixture C) indicated by the dried spot of the red dye Ponceau S, (b) label incorporated portion 35 (point of application of Mixture B) including radiolabeled thyroxine, (c) specific binding partner incorporated portion 36 (point of application of Mixture A) including immobilized antibody to thyroxine, and (d) terminal end portion 37 (point of application of Mixture D) including, as indicator means, a combination of an acid and a pH indicator which produces a color change upon contact by an alkaline liquid.

B. Assay Method

Ten (10) μl of a serum sample to be tested is applied to the sample receiving portion 34 of a test device 30. The test device 30 is then placed, with the beginning end portion 33 down, in a test tube 41 (FIG. 8) containing 1 ml of the developing solution. The size of the test tube is selected so that the developing solution contacts the test device 30 only at its beginning end portion 33, with no contact with its terminal end portion 37 (as depicted in FIG. 8). The test tube is capped and allowed to stand at room temperature until a color change from yellow to blue is observed at terminal end portion 37 (about one hour). At such time, all of the developing fluid in the test tube will have been drawn up into the strip element 31 of the test device 30. The test tube is then inverted, all but ½ inch (12.2 mm) of the test device measured from the fold of the paper strip is shrouded by inserting each tube into a length of ⅝ inch (16 mm) O.D. copper tubing, and the tube is placed into the counting well 52 (FIG. 9) of an In-V-Tron 200 gamma counter (manufactured by Nuclear Systems, Inc., Garland, Texas) to measure the amount of gamma radiation emitted at and proximate to the specific binding partner portion 36 of the test device.

C. Principle of Test

As the developing fluid is transported up strip element 31 by capillarity, the serum sample applied at portion 34 is encountered first. The advancing developing fluid carries the serum sample, including any thyroxine present therein, to the label incorporated portion 35. Endogenous non-radioactive thyroxine is mixed with labeled thyroxine as the developing fluid advances towards the fold of strip element 31. The thyroxine mixture is carried over the fold in strip element 31 by the developing fluid and then comes into contact with antiserum to thyroxine which is immobilized at portion 36. As the thyroxine mixture moves through portion 36, endogenous non-radioactive thyroxine and labeled thyroxine compete for antibody binding sites. Once the thyroxine mixture has passed through portion 36, the amount of labeled thyroxine bound to immobilized antibody, and thereby itself immobilized at portion 36, is inversely related to the amount of thyroxine present in the serum sample. Complete traversal of strip element 31 by the developing fluid is indicated by a color change in terminal end portion 37 which results upon wetting by the developing fluid.

D. Results

The assay procedure was run in duplicate on two (2) serum samples having known thyroxine contents (Thyroid Profile Control Sera from Oxford Laboratories, Inc., Foster City, CA). The results were as follows:

| Type of Serum Control | Normal Control | Elevated Control |
|---|---|---|
| Lot Number | 14221 | 14222 |
| Stated Thyroxine Content | 6.2 ± 0.6 μg/100 ml | 13.9 ± 0.7 μg/100 ml |
| Counts/min (thousands) | 13.71, 13.51 | 9.56, 9.70 |
|  | av. 13.61 | av. 9.63 |

These data indicate that the amount of labeled thyroxine resulting at and proximate to the fold of the test device after traversal of the strip element by the developing fluid is an inverse function of the amount of thyroxine present in the serum sample tested.

EXAMPLE 2

Test for the Triiodothyronine Binding Capacity of Serum

A. Preparation of Test Devices

Blank test devices were prepared by cutting paper strips and folding them over and affixing them to plastic strips in the manner described in Part A of Example 1.

The following liquid mixtures were prepared:

Mixture E—A mixture of:
(1) 9.12 g citric acid monohydrate,
(2) 14.12 g trisodium citrate dihydrate, and
(3) deionized water sufficient to make a total volume of 1 liter.

Mixture F—An aqueous solution containing 10 mg of red dye Ponceau S per 100 ml.

Mixture G—A mixture of:
(1) 100 microcuries $^{125}$I-labeled triiodothyronine (obtained from Cambridge Radiopharmaceuticals Corp., Billerica, MA) in 1 ml of 50% propylene glycol;
(2) 20 ml of a 100 ml aqueous solution containing 5.32 sodium barbital, 1.44 ml 2 N hydrochloric acid, and 1 mg crystal violet;
(3) 50 μl of an aqueous solution containing 50 mg gentamicin per ml; and
(4) 50 μl of an aqueous solution containing 250 mg human serum albumin per ml.

Mixture H—A mixture of:

(1) 50 mg hydroxypropyl guar gum (Jaguar HP-11 brand from Stein-Hall Specialty Chemical, New York, NY);
(2) 2 g microfine precipitated silica (QUSO 32 brand from Philadelphia Quartz Co., Valley Forge, Pa.);
(3) 0.1 ml of an aqueous solution of 500 mg crystal violet per 100 ml; and
(4) 150 ml of Mixture E.

Mixture J-An aqueous solution containing 0.02 M sodium hydroxide and 50 mg/100 ml bromcresol purple.

The above liquid mixtures were then applied dropwise to the paper strips as follows:

| Mixture | Volume (μl) | Point of application measured from beginning end of strip (mm) |
| --- | --- | --- |
| F | 10 μl | 35 |
| G | 10 μl | 54 |
| H | 30 μl | 108 |
| J | 10 μl | 185 |

The strips were allowed to dry at room temperature.

Mixture E was used as the developing fluid.

Referring to FIGS. 5-7 of the drawing, the resulting test devices 30 each included (a) sample receiving portion 34 (point of application of Mixture F) indicated by the dried spot of the red dye Ponceau S, (b) label incorporated portion 35 (point of application of Mixture G) including radiolabeled triiodothyronine, (c) binding agent incorporated portion 36 (point of application of Mixture H) including immobilized silica capable of adsorbing free triiodothyronine but not triiodothyronine bound to serum proteins, and (d) terminal end portion 37 (point of application of Mixture J) including, as indicator means, a combination of an alkali and a pH indicator.

B. Assay Method

The same procedure as described in Part B of Example 1 was followed.

C. Principle of Test

As the developing fluid is transported up strip element 31 by capillarity, the serum sample applied at portion 34 is encountered first. The advancing developing fluid carries the serum sample to the label incorporated portion 35 where it is mixed with labeled triiodothyronine. The thyroxine binding globulin present in the serum sample binds an amount of the labeled triiodothyronine proportional to the degree of its unsaturation. When the resulting mixture is passed through binding agent incorporated portion 36, free labeled triiodothyronine, i.e. that not bound to thyroxine binding globulin, is adsorbed by the immobilized silica particles. Upon complete traversal of strip element 31 by the developing fluid, the amount of labeled triiodothyronine immobilized at portion 36 is directly related to the percent saturation of thyroxine binding globulin in the serum sample.

D. Results

The assay procedure was run in duplicate on two (2) serum samples having known triiodothyronine binding capacities (expressed as T-3 percent uptake) (control sera from Lederle Diagnostics, Pearl River, NY).

The results were as follows:

| Type of Serum Control | "RIA Control I" | "RIA Control II" |
| --- | --- | --- |
| Lot Number | 2945-301 | 2946-301 |
| Stated T-3 Percent Uptake | 42.0 | 68.9 |
| Counts/min (thousands) | 10.35, 11.49 | 18.60, 18.02 |
|  | av. 10.92 | av. 18.31 |

These data indicate that the amount of labeled triiodothyronine resulting at and proximate to the fold of the test device after traversal of the strip element by the developing fluid is a direct function of the percent saturation of triiodothyronine binding proteins in the serum sample tested.

EXAMPLE 3

Test for Folic Acid and Analogues Thereof in Serum

A. Preparation of Test Devices

Blank test devices were prepared by cutting paper strips and folding them over and affixing them to plastic strips in the manner described in Part A of Example 1.

The following liquid mixtures were prepared:

Mixture K-A 150 ml aqueous solution containing 100 mg Baker gelatin (obtained from Doe and Ingalls Co., Medford, MA), 500 mg 2-amino-2-(hydroxymethyl)-1, 3-propanediol, 100 mg ascorbic acid, 67 mg sodium azide and 0.383 ml 1 N sodium hydroxide.

Mixture L-A 20 ml volume of Mixture K containing 20 mg beta-lactoglobulin (obtained from Sigma Chemical Co., St. Louis, MO).

Mixture M-A 0.5 ml volume of Mixture K containing 1.2 microcuries of $^{125}$p-labeled folic acid (obtained from Diagnostic Biochemistry Inc., San Diego, CA).

The above liquid mixtures and Mixture D from Example 1 were then applied dropwise to the paper strips as follows:

| Mixture | Volume (μl) | Point of application measured from beginning end of strip (mm) |
| --- | --- | --- |
| L | 20 | 92 |
| M | 10 | 80 |
| D | 10 | 185 |

A light pencil mark was also made on each paper strip at a point 67 mm from the beginning end thereof. The strips were allowed to dry at room temperature.

Mixture K was used as the developing fluid.

Referring to FIGS. 8 and 9 of the drawing, the resulting test devices 30 included (a) sample receiving portion 34 (indicated by the pencil mark), (b) label incorporated portion 35 (point of application of Mixture M) including radiolabeled folic acid, (c) specific binding partner incorporated portion 36 (point of application of Mixture L) including beta-lactoglobulin, and (d) terminal end portion 37 (point of application of Mixture D) including, as indicator means, a combination of an acid and a pH indicator.

B. Assay Method

The same procedure as described in Part B of Example 1 was followed.

C. Principle of Test

As the developing fluid is transported up strip element 31 by capillarity, it entrains first the serum sample and then the radiolabeled folic acid. The folic acid and its analogues present in the sample and the radiolabeled folic acid become mixed as the developing fluid advances to the binding partner incorporated portion 36. Beta-lactoglobulin has a limited ability to bind folic acid and its analogues and therefore as the sample/label mixture passes through portion 36, a fraction of the amount of folic acid and its analogues in the mixture become bound to beta-lactoglobulin. As the developing fluid advances upward and over the fold in strip element 31, the beta-lactoglobulin/folic acid or analogue complexes formed are transported along strip element 31 but at a rate that is less than the rate of transport of free folic acid and its analogues. Portions 36 of strip element 31 is positioned such that upon complete traversal of strip element 31 by the developing fluid, substantially all of the beta-lactoglobulin/labeled folic acid complexes that have formed are disposed at or proximate to the fold of strip element 31. Free labeled folic acid meanwhile has been transported to the terminal end portion 37. Therefore, the amount of radiolabeled folic acid resulting at and proximate to the fold of strip element 31 is inversely related to the amount of folic acid and its analogues in the serum sample.

D. Results

The assay procedure was run in duplicate on two (2) serum samples having known folate contents (control sera from Lederle Diagnostics, Pearl River, NY). The results were as follows:

| Type of Serum Control Lot Number Stated Folate Content (as determined by three different methods) | "RIA Control I" 2945-301 | "RIA Control II" 2946-301 |
| --- | --- | --- |
| 1st Method | 4.0 mg/ml | 3.8 mg/ml |
| 2nd Method | 3.6 mg/ml | 2.9 mg/ml |
| 3rd Method | 2.5 mg/ml | 2.2 mg/ml |
| Counts/min (thousands) | 5.92, 6.06 av. 5.99 | 8.49, 8.02 av. 8.26 |

These data indicate that the amount of labeled folic acid resulting at and proximate to the fold of the test device after traversal of the strip element by the developing fluid is an indirect function of the amount of folate in the serum sample tested.

Obviously, many other modifications and variations of the invention as set forth hereinabove may be made without departing from the spirit and scope thereof.

What is claimed is:

1. A test strip for determining a characteristic of a sample, comprising a length of material capable of transporting a developing liquid therealong by capillarity, said strip including
   a first end, at which capillary transport begins;
   a second end, at which capillary transport ends;
   a plurality of zones positioned between said first and second ends, said zones including
   a first zone for receiving said sample,
   a second zone impregnated with a first reagent capable of being transported along said strip by said developing liquid,
   a third zone downstream of said first and second zones impregnated with a second reagent,
   said first and second zones being spaced sufficiently from said first end to permit contact of said first end but not said first and second zones with said developing liquid,
   said first reagent being capable of reacting with one of the following group consisting of (1) said sample, (2) said sample and said second reagent, and (3) said second reagent in competition with said sample, to form a product in an amount dependent on said characteristic being determined,
   one of the group consisting of said second reagent and said material being a retarding element capable of slowing capillary transport of a moving element, said moving element being one of the group consisting of said product and said first reagent to thereby separate said product from said first reagent, and
   said first reagent having a detectable property that provides a label for said first reagent and for said product to permit one of them to be a detectable agent whose amount is to be detected; and
   a measuring location at or downstream of said third zone,
   said measuring location being spaced upstream of said second end a distance preselected so that, when transport of said developing liquid along said strip element is terminated by the leading front thereof reaching said second end, said product and said first reagent have been separated sufficiently to permit the amount of said detectable agent to be detected at said location by measuring said detectable property,
   whereby, after said sample is placed on said first zone and said first end is dipped into said developing liquid, said developing liquid transports said sample and first reagent to bring about the reaction to form said product, in an amount dependent on said characteristic; said retarding element slows transport of said moving element to spatially separate the two; and the amount of said moving element and thereby said characteristic, is measured at said measurement location by measuring said detectable property.

2. A test strip according to claim 1 further comprising an inert support to which said strip is affixed.

3. A test strip according to claim 2 wherein said support is a sheet laminated to said strip, the support sheet having a width about the same as that of said strip and a length greater than one-half of, but less than the length of said strip, the transverse edge of said first end being about co-extensive with one end of said support and said strip being folded transversely over the other end of said support so that the transverse edge of said second end is spaced from said first end.

4. A test strip according to claim 3 wherein the third zone is at or proximate to the fold of said strip.

5. A test strip according to any of preceding claims 1-3 further provided with indicator means at said second end, responsive to contact with said developing liquid for indicating when the developing liquid has reached the second end.

6. A test strip according to any one of claims 1 to 3 for detecting the binding capacity for a first ligand of a sample which contains a second ligand in free and bound forms, wherein the first reagent includes a labelled form of the first ligand, and the second reagent comprises a binding agent capable of binding said labelled form of the first ligand when in one of said free form and said bound form but not when in the other, said labelled form and said binding agent being incorporated in said strip in their respective zones in proportions such that an amount of said product is produced, which is a function of the ligand binding capacity of said sample.

7. A test device comprising a sealable chamber in which a test strip according to any one of claims 1-3 is held upright therein with said first end of said length of material immersed in said developing ligand.

8. A test strip according to claim 1 for quantitatively determining a ligand ingredient in a sample, wherein said first reagent comprises a labelled form of said ligand or of a specific binding analog thereof, the ligand and binding analog respectively being capable of reacting in competition with the ligand in the sample, with a second reagent which comprises a specific binding partner of said ligand, said labelled form and said binding partner being incorporated in said strip in their respective zones in proportions such that an amount of said product is produced which is a function of the amount of said ligand in said sample.

9. A test strip according to claim 8 wherein said labelled form is a radioactive form of said ligand or of said binding analog respectively.

10. A test strip according to claim 1 for determining quantitatively protein(s) in a liquid sample, wherein said second reagent comprises an agent for coupling said first reagent to protein(s) to provide labelled proteins.

11. A test strip according to claim 10 for determining a particular protein quantitatively, in which said measuring location is positioned to measure the amount of coupled product transported by said developing liquid when said developing liquid reaches said second end.

12. A test strip according to claim 10 or 11 wherein said first reagent is radioactive iodide.

13. A test strip according to claim 1 for quantitatively determining in a liquid sample a first substance which reacts with a second substance to produce hydrogen peroxide wherein said first reagent comprises radioactive iodide and said second reagent comprises said second substance.

14. A test strip according to claim 13 for quantitatively determining in a liquid sample a substrate for an oxidase enzyme reaction which produces hydrogen peroxide, wherein said second substance comprises said oxidase enzyme.

15. The test strip of claim 1 wherein said detectable property is radioactivity.

16. The test strip of claim 1 wherein
said first reagent is selected to react with said sample to form an amount of said product that is dependent on said characteristic and
said second reagent is selected to slow transport of the portion said first reagent unreacted with said sample.

17. The test strip of claim 1 wherein
said first reagent is selected to be mixable with said sample and transportable therewith to said third zone and
said second reagent is selected to react in said third zone with at least said sample to form said product.

18. The test strip of claim 17 wherein
said second reagent reacts with said sample and said first reagent in said third zone and
said first reagent is selected to be sufficiently chemically similar to an ingredient of said sample as to complete with said ingredient in reacting with said second reagent to form said product,
whereby the amount of said product is dependent on the amount of ingredient competing therewith in reacting with said second reagent.

19. The test strip of claim 18 wherein said second reagent slows transport of said product.

20. The test strip of claim 17 wherein
said second reagent reacts with said sample and said first reagent to form said product.

21. The test strip of claim 20 wherein transport of said product is slowed by said material.

* * * * *